(12) United States Patent (10) Patent No.: US 6,290,659 B1
Hill (45) Date of Patent: Sep. 18, 2001

(54) SKIN EXFOLIATION METHOD AND APPARATUS

(76) Inventor: John M. Hill, 750 65th St., South, St. Petersburg, FL (US) 33707

(*) Notice: Subject to any disclaimer, the term of this patent is extended or adjusted under 35 U.S.C. 154(b) by 0 days.

(21) Appl. No.: 09/407,585

(22) Filed: Sep. 28, 1999

Related U.S. Application Data

(60) Provisional application No. 60/126,612, filed on Mar. 27, 1999, and provisional application No. 60/129,166, filed on Apr. 14, 1999.

(51) Int. Cl.$^7$ .................................................... A61F 13/00
(52) U.S. Cl. ............................... 601/17; 602/41; 602/42; 602/43; 602/44; 602/45; 602/46
(58) Field of Search ............................. 601/17; 424/401, 424/443; 602/41–47

(56) References Cited

U.S. PATENT DOCUMENTS

| | | | |
|---|---|---|---|
| 4,659,740 | * | 4/1987 | Usher . |
| 4,699,930 | * | 10/1987 | Suga . |
| 5,720,963 | | 2/1998 | Smith .................................. 424/401 |

OTHER PUBLICATIONS

Specification sheet, Type 375 Scotch Brand Superior Performance Box Sealing Tape, 3M Corporation, St. Paul MN, no date.
Specification sheet, Type 3565 Highland Brand Utility Label Protection Tape, 3M Corporation, St. Paul MN, no date.
"3 Step. Take the Test. Get the Answers.", Clinique Laboratories, Inc., internet page http://www.clinique.com/app/UK/9901tapetest.html, Apr. 17, 1999.

* cited by examiner

Primary Examiner—Michael A. Brown
Assistant Examiner—Lalita M. Hamilton
(74) Attorney, Agent, or Firm—David Kiewit

(57) ABSTRACT

An immediate and visible temporary cosmetic improvement in skin condition is obtained by a multi-stage exfoliation method having a visible end point and providing a margin of safety so that the user's skin is not significantly irritated if he or she ignores the end point and continues to carry out additional and unnecessary exfoliation steps. The preferred method involves repeatedly attaching transparent exfoliation sheets having a pressure sensitive adhesive to a selected part of the user's body and then removing each sheet by grasping one edge and pulling it across the rest of the sheet. A handle may be detachably adhered to each sheet for superior results. After each repetition the user inspects the sheet that has just been removed to monitor the amount of exfoliated tissue. When the amount of tissue on a sheet is discernibly less than that removed in the immediately previous repetition, the process is completed. Alternately, a user may compare each removed sheet with a prefabricated comparison sheet that shows a number of visually distinct regions representative of various amounts of exfoliated tissue and from this may recreate and set an individualized target end point that conforms to his or her specific desires and limitations for exfoliation. A set of precut exfoliation sheets shaped to fit a selected portion of the body may be sold in a kit that also includes a prefabricated comparison sheet, and a rod-like handle that can be attached to an edge of each of the sheets for application.

19 Claims, 2 Drawing Sheets

SKIN EXFOLIATION METHOD AND APPARATUS

CROSS REFERENCE TO RELATED APPLICATIONS

This application claims the priority date of U.S. Provisional Application for Patent 60/126,612, filed Mar. 27, 1999 and of U.S. Provisional Application for Patent 60/129,166, filed Apr. 14, 1999.

STATEMENT REGARDING FEDERALLY SPONSORED R&D

Not applicable

BACKGROUND OF THE INVENTION

1. Field of the Invention

The invention relates to cosmetic treatments for temporarily improving the surface texture of human skin. More specifically, the invention relates to treatments involving the removal of, or that promote the removal of, outer layers of the epidermis.

2. Background Information

Many approaches have been proposed and used for removing blemishes from and for improving the surface texture of the face and other portions of the human body by removing an outer portion of the epidermis. Known approaches include those of a surgical or quasi-surgical nature and include dermabrasion and laser surgery. Approaches of particular interest to the present invention are adhesive exfoliation methods in which an outer portion of the skin is peeled off after being adhered to some substance or another. In some of these approaches (commonly called "face masks" or "beauty masks") a liquid or viscous adherent material is applied to the portion of the body to be exfoliated and is allowed to dry or set up. When the dried or solidified material is peeled off the body some dead surface tissue is removed from the skin. Another adhesive exfoliation technique is generally known as "tape stripping" and involves adhering a tape having a pressure-sensitive adhesive backing to the user's body and then pulling the tape off the body part to remove an outer layer of skin.

Some of the more popular approaches to exfoliation are chemical in nature and involve application of an exfoliant material that attacks the outer layers of the skin. These chemical approaches include, inter alia, retin-A, glycolic acid and alpha hydroxy acid "peels". A notable variation on this theme is the use of pre-cut segments of an adhesive coated tape in which an exfoliant material has been incorporated into the adhesive. These products, which include the Sudden-Change® Hydroxy-Patch distributed in the US by CCA Industries, Inc. of East Rutherford N.J., use a generally weak adhesive to hold the active chemical ingredients in contact with a user's skin for the duration of a treatment period, which may extend over the greater part of an hour.

Of particular note is U.S. Pat. No. 5,720,963 wherein Smith teaches a variety of long term skin treatments, several of which include a regime of five to ten tape stripping steps repeated twice daily in order to chronically disrupt a skin water barrier. Smith also teaches that more severe treatments can be carried out less frequently (e.g., every second or third day) by using a more aggressive skin-adhering adhesive, such as a cyanoacrylate adhesive. Although he discloses several different tape stripping approaches in U.S. Pat. No. 5,720,963, Smith states that his tape stripping method has numerous drawbacks, which include a wide range of response of various individuals to tape stripping, as well as a stated need for an expensive laboratory instrument to monitor the process. Moreover, Smith's teaching is directed entirely towards treatments extending over several months before obtaining discernible results. He does not teach any methods that result in immediate improvements associated with tape stripping.

In another discussion of tape stripping, which is found in a promotional writing for a line of exfoliation soaps and lotions sold by Clinique Laboratories Inc., a single tape stripping of skin on the back of the consumer's hand is proposed as a diagnostic test. This test is preferably carried out using a piece of transparent adhesive tape on which the user can view the removed tissue to solely demonstrate the presence of easily exfoliated dead skin.

BRIEF SUMMARY OF THE INVENTION

One feature of the invention is an immediate and visible improvement in skin condition that is preferably obtained by a multi-stage exfoliation method having a visible end point and providing a margin of safety whereby the user's skin is not significantly irritated if the user ignores the end point and continues to carry out additional and unnecessary exfoliation steps.

A preferred method of practicing the skin exfoliation method of the invention comprises the steps of: 1) preparing a transparent exfoliation sheet having an adhesive-covered portion comparable in size and shape to a portion of the user's body that is to be exfoliated and attaching a handle along one edge of the sheet; 2) adhering that portion of the exfoliation sheet immediately adjacent the handle to a first edge of the predetermined portion of the body; 3) rubbing or pressing on the exfoliation sheet by moving one's hand or fingers from a staring position adjacent the handle toward that edge of the exfoliation sheet distal from the handle so as to attach substantially the entire sheet to the predetermined portion of the body by means of the pressure sensitive adhesive; 4) grasping the handle and pulling it along the surface of the predetermined portion of the body so as to separate the first exfoliation sheet from the portion of the body being exfoliated; 5) visually examining the removed first transparent exfoliation sheet to determine the amount of skin exfoliated; 6) preparing a new exfoliation sheet and repeating steps 1) through 5) until the amount of exfoliated skin noted at an ending repetition is discernibly less than the amount of exfoliated skin retained on the respective exfoliation sheet employed in the immediately preceding repetition. This method of exfoliation allows the user to successfully maintain smoother skin and reduce the size of blemishes while avoiding irritation.

Another method of the invention, useful when only small blemishes are present, comprises a similar iterative process wherein a user repeatedly adheres a new sheet of adhesive-coated film to a predetermined portion of his or her skin and then pulls each film off until observing that the blemish has been removed.

In a further aspect, the invention provides a skin exfoliation kit for use on one's face or on some other predetermined portion of the body. This kit may comprise a plurality of pressure sensitive adhesive-coated exfoliation sheets, which are preferably transparent. Each of the sheets preferably has a size and shape adapted to the predetermined portion of the body. Each of the adhesive-coated sheets in a preferred kit has at least one protective backing sheet temporarily adhered to its adhesive coated surface. Removing a backing sheet exposes most of the pressure sensitive adhesive—i.e., the working fraction of the adhesive that can be used for skin exfoliation. In some cases two protective backing sheets are used, with the smaller of two backing sheets disposed over an edge portion of the exfoliation sheet. In these cases, when the smaller backing sheet is removed an exfoliation sheet handle can be attached adjacent one edge of the sheet.

In yet a further embodiment of the invention, an exfoliation kit may comprise one or more transparent comparison sheet(s) displaying a plurality of regions having differing appearance. The appearance of each of the regions is selected to be respectively representative of a predetermined amount of exfoliated skin, and the regions are preferably arranged in a row so that a region representative of a minimal amount of exfoliated tissue at one end of the row and one representative of a maximal amount of exfoliated tissue at the other end. A user may select one of these regions as a target representative of a desired end point In subsequent exfoliation operations the user can then compare the amount of exfoliated tissue adhering to each of a series of exfoliation sheets as the each sheet is removed and can terminate the process when the visual appearance of the most recently removed sheet matches that of the target.

Thus, one feature of the invention is that it provides a skin care kit comprising a plurality of exfoliation sheets and an exfoliation sheet handle selectively attached to ones of the plurality of sheets.

Yet another feature of the invention is the provision of a plurality of sections of transparent pressure sensitive exfoliation sheets that can be viewed sequentially in transmitted illumination to allow a user to monitor progress during a skin exfoliation process.

Preferred methods described herein provide a means of detecting an end point to avoid irritation of the skin while obtaining the best cosmetic results in an iterative exfoliation process, and do so without any need for expensive laboratory apparatus for monitoring.

Although it is believed that the foregoing recital of features and advantages may be of use to one who is skilled in the art and who wishes to learn how to practice the invention, it will be recognized that the foregoing recital is not intended to list all of the features and advantages, Moreover, it may be noted that various embodiments of the invention may provide various combinations of the hereinbefore recited features and advantages of the invention, and that less than all of the recited features and advantages may be provided by some embodiments.

DETAILED DESCRIPTION OF THE INVENTION

Figure 1:
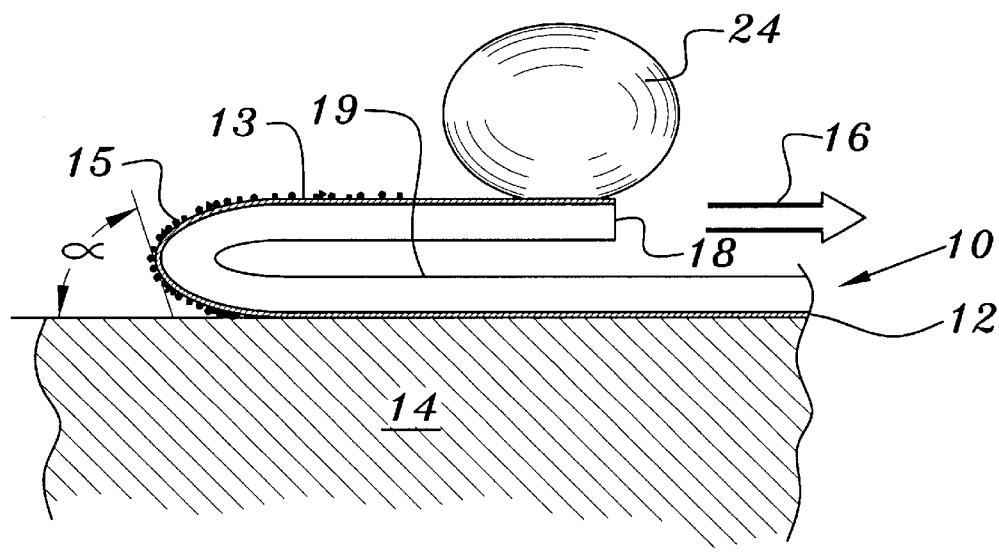
FIG. 1 is a partly elevational view depicting a stage in a skin exfoliation process.
Figure 2:
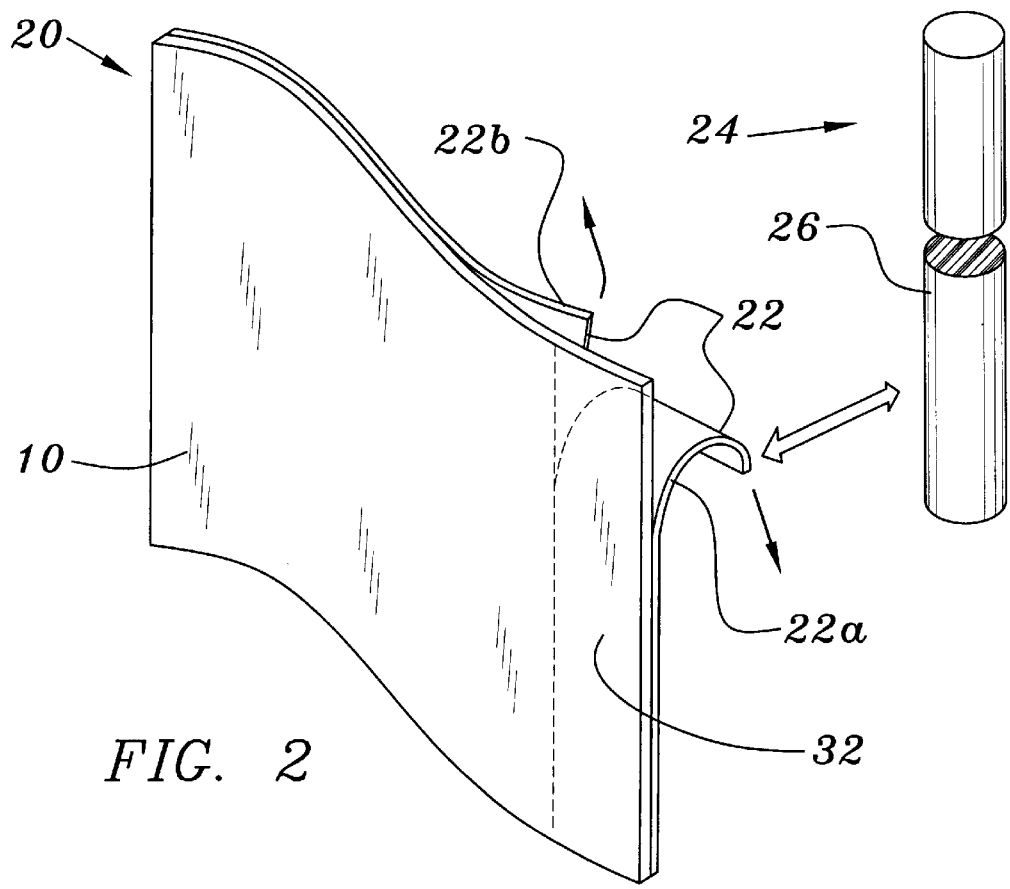
FIG. 2 is a partly exploded view of a pre-cut transparent exfoliation sheet with a protective backing sheet and an attachable handle.
Figure 3:
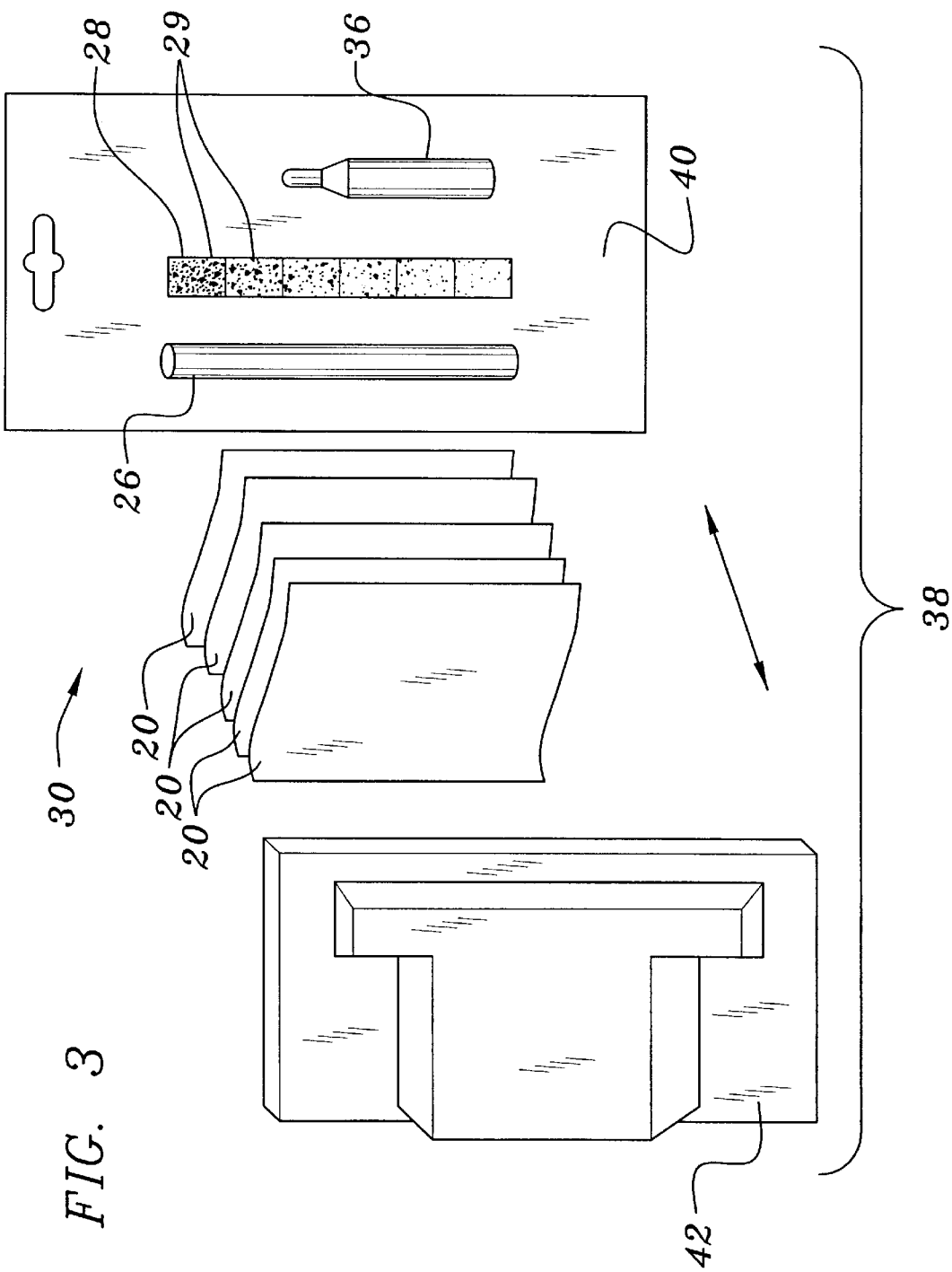
FIG. 3 is an exploded view of an exfoliation kit of the invention.

An adhesive exfoliation process, as discussed above, may comprise the use of a flexible exfoliation film or tape 10 having a layer of a pressure-sensitive adhesive 12 disposed on only one side 13 thereof As is well known, this adhesive may be used to adhere a portion of the film 10 to a predetermined portion of a user's body 14 so that when the film 10 is removed (e.g., by pulling the sheet back along itself from one edge, as is depicted in FIG. 1 with the twin-tailed arrow 16), a strippable portion of the user's epidermis 15 adheres to the adhesive film and is thereby lifted away from the user's body 14.

A method of exfoliation that is used for removal of small blemishes is iterative in nature and calls for the use of a plurality of portions of an exfoliation film 10, with a new sheet of the film 10 being used in each iteration. This plurality of portions of film 10 may comprise a plurality of pre-cut sheets 20, each of which has one or more backing sheets 22 initially disposed on its adhesive-coated side 13. After a first sheet is pulled away from the predetermined portion of a user's body, the user practicing the preferred method visually examines the portion of his or her body that is being exfoliated to see if the blemish has been removed. If not, the process is repeated.

In a preferred method of the invention, transparent exfoliation sheets 10 are used and after each exfoliation of a predetermined area the user visually inspects the sheet 10 to assess the amount of exfoliated tissue adhering to that sheet This inspection is preferably done by using bright transmitted light. A second sheet is then employed in the same fashion as the first, and the amount of tissue lifted away with the second sheet is compared with that lifted with the first sheet. These steps of applying an exfoliating sheet 10, pulling it away from the body, and determining the amount of tissue exfoliated are repeated until the user observes that the amount of tissue adhering to the sheet at a given iteration is discernibly less than that adhering to the sheet used in the immediately preceding iteration. When this occurs, the exfoliation process is completed. The method described above promotes immediate, optimal cosmetic improvements while at the same time preventing excessive epidermal loss, which can lead to undesirable irritation.

The end points of the processes recited above are user-specific. Both the amount of tissue exfoliated in each of the first few iterations, and the optical density at which a visually discernible drop off in density is observed have been found to vary widely from individual to individual. However, for any given individual the visually discernible drop off in optical density has been found to occur at about the same optical density on each of his or her uses of the process. Hence, it is possible for an individual to select a particular optical density, representative of a respective amount of tissue, on the exfoliation sheet and to use that to set his or her end point.

After the user has determined an end point that is satisfactory for his or her use of the exfoliation process, he or she may compare the sheet 10 that was removed at the end point of the process with a transparent comparison strip 28 that preferably has a plurality of discrete, visually distinct regions 29 representative of varying amounts of exfoliated tissue. The user can select, as a target for subsequent exfoliations, that one of the patterned regions that most closely visually matches the sheet that he or she removed at his or her end point—i.e., that matches the density of exfoliated tissue at the point at which the amount of tissue exfoliated in each repetition of the process begins to fall off The next time the user chooses to use the iterative exfoliation process of the invention, the end point can be obtained by visually matching each used exfoliation sheet 10 with a chosen target region 29 on a comparison strip until a close match occurs. This matching process is believed to be simpler and easier than is the initial process of comparing amounts of exfoliated tissues on sequential ones of a series of freshly removed sheets.

The visually distinct regions 29 on the comparison strip 28 may comprise printed indicia (e.g., as made by a silk screening operation), or may be embossed or otherwise formed on a transparent substrate. The comparison strip 28 may be prepared from images of a series of used exfoliation sheets, where each of the images shows a differing amount of exfoliated tissue, and where each of the images is preferably selected from a portion of the respective sheet having no extraneous structural detail such as wrinkles, skin blemishes, etc. That is, each of the images is selected to represent a different visually discernible density of removed tissue. The sequence of images may then be reproduced on a transparent substrate by known means, such as embossing or screen printing, so as to form a sequence of patterned regions 29 running from a densest to a least dense region. Although the drawing depicts a single, separate comparison strip 28 supplied as a portion of an exfoliation kit 30, it will be understood by those skilled in the art that one could choose to supply an array of patterned regions 29 as an edge portion of each exfoliation sheet. For example, one could screen a pattern of indicia onto a strip running along the edge of each sheet before coating the sheet with adhesive. In this arrangement, one would preferably leave the comparison portion of the sheet free of adhesive so as to avoid exfoliating skin onto the comparison portion, which would degrade the visual quality of the pattern of indicia during exfoliation.

The exfoliation methods taught herein are believed to be much less likely to cause irritation than are approaches using exfoliant chemicals. In following the processes of the invention the user will note that the tenacity of adhesion of sequential ones of the sheets will begin to slowly fall off at about the same time that the user's tactile sensitivity to the exfoliation process begins to slowly increase with further exfoliation steps. Both the onset of minor irritation and the loss of tenacity occur when substantially all of the of the dry, dead portion of the skin has been removed and a moist skin layer is revealed. Thus, various methods of the invention comprise at least three different discernible end points: visible removal of a blemish; a visible decrease in the exfoliated amount of tissue on a film; and a noticeable decrease in tenacity of the adhesive to the skin.

The exfoliation processes described above have been found to be more effective when a parting angle (denoted with the Greek letter $\alpha$ in FIG. 1) is maximized by pulling the initially detached edge 18 of the sheet along that portion of the body still covered with the balance of the sheet. That is, the amount of exfoliated tissue 15 is increased by removing the sheet 10 while holding the detached edge 18 in contact with, or as close as possible to, the adhesive-free surface 19 of the sheet 10. Removing the sheet 10 at a more acute parting angle (e.g., by pulling perpendicular to the body instead of pulling along the sheet-covered portion) results in the exfoliation of less tissue. It may be noted that the sheet 10 is depicted in FIG. 1 as being unrealistically thick so that various portions of the sheet can be more clearly pointed out. The preferred approach thus reduces both the number of sheets used and the number of times a user must apply sheets.

As noted above, inspection of the exfoliation sheet or film to determine a process end point by monitoring the amount of material removed is most conveniently carried out with exfoliating films having a high degree of transparency. This allows the user to easily and clearly inspect the used exfoliation sheets in transmitted light. It will, however, be recognized that no film is perfectly transparent, and that a reasonable range of actual measured transparencies are encompassed in commercially available materials that are labeled as being transparent. Moreover, it will be recognized that lightly colored sheets (e.g., those prepared from some commonly available brown packing tapes), as well as those having a matte finish on the adhesive-free side, are sufficiently transparent that a user can inspect a used exfoliation sheet made from one of these materials in transmitted light. Additionally, it will be realized that even if one uses an opaque sheet, it is nonetheless possible, albeit less effective, to inspect the adhesive-coated side of an opaque used exfoliation sheet in order to determine the amount of tissue exfoliated.

It may be noted that a preferred exfoliation sheet 10 comprises a piece of a pressure-sensitive transparent tape of the sort commonly used for sealing packages to be shipped by the postal service or by another common carrier. Many sorts of pressure-sensitive transparent tapes may be used to practice the invention. A preferred tape, comprising a pressure sensitive hot melt rubber resin on a biaxially oriented polypropylene film base, is sold by the Masking and Packaging Systems Division of the 3M Corporation as Scotch™ Brand Type 375 Box Sealing Tape. This tape has an adhesion to steel of fifty five ounces per inch of tape width, as measured by ASTM Test D-3330. Another polypropylene film tape, having a pressure sensitive adhesive, that has been used successfully, is a similar product having a somewhat lower adhesion to steel. This product is sold by the 3M Corporation as their Highland™ Brand Type 3565 Utility Label Protection Tape.

Although it is possible to apply and remove exfoliation sheets without the use of tools, when doing so the user's fingers tend to stick to the film, thus making it harder to apply. To overcome this difficulty, a rigid rod 26 (e.g., a common wood-bodied pencil) was attached to that edge of the sheet that was to be removed first. This allowed the sheet to be handled without the user's fingers contacting the adhesive The inventor found that the use of a handle 24 dramatically reduced wastage of sheets that had previously occurred when a sheet that was being handled turned back upon itself so that two portions of the adhesive-coated surface came into contact with each other, causing adhesive-to-adhesive binding, which effectively destroyed that sheet. In addition, the presence of the handle 24 made removal of the sheet 10 both more uniform and more comfortable than had been the case when the sheet was grasped with the fingers at several points along an edge and pulled away from the body. That is, removing the sheet without the handle 24 often led to the sheet twisting and bunching, which in turn could lead to an uncomfortable removal. Moreover, the handle 24, which preferably extends along one entire edge of a sheet, helps the user to align and place the sheet over a selected portion of his or her body. This is especially true for the facial region. Although a preferred handle means 24 comprises a rigid cylindrical rod 26, it will be understood that many different sorts of handle means may be employed in practicing the exfoliation method of the invention. One could employ a spatulate stick, a generally flat plastic tab, or any other object that could be conveniently and temporarily attached to the exfoliation sheet.

A exfoliation kit 30 can be prepared from the preferred tape 10 by adhering one or more easily removed backing sheets 22a, 22b to each of a plurality of exfoliation sheets cut to fit a predetermined portion of a user's body. For example, for exfoliating a person's facial region, sheets having dimensions of roughly five and one half inches by nine inches can be cut from a roll of the Type 3565 tape and suitable backing sheets can be detachably adhered thereto.

In carrying out a preferred method of facial skin exfoliation using the kit 30, a user may select one of the pre-cut exfoliation sheets 20 from the kit 30 and remove a first, narrow, backing sheet 22a from an edge portion 32 of the sheet 20. A rod 26 may then be adhered to the sheet 12 and used to hold the one edge of the sheet 20 while the second backing sheet 22b is detached from the balance of the adhesive coated surface of the exfoliation sheet. The user then preferably places the rod along the vertical mid-line of his or her face, and gently rubs the adhesive-free surface 42 of the exfoliation sheet 20 from the rod toward the other end of the sheet—i.e., from the midline of his or her face toward a lateral margin thereof. After the sheet 12 is well adhered to the face, the user grasps the rod 26 and pulls it toward the lateral margin of the face. This is preferably done while holding the rod 26 as close to the adhesive free surface 34 as is practical, as depicted in FIG. 1.

In exfoliating the skin on a person's face, it is convenient to use a single complete sheet large enough to extend from the chin to the hairline in one direction and from the midline of the face at the bridge of the nose to the inner edge of the ear in a transverse direction, and to select a handle having approximately the same length. This use of a large sheet allows the user to maximize the area being exfoliated while allowing continued and uninterrupted vision and respiration during the process. In using a large exfoliation sheet of this sort, a preferred exfoliation method calls for rubbing a small amount of a lubricant, such as petroleum jelly or other lubricant, onto the eyelids, eyebrows and other hair-covered portions of the body that may come in contact with the adhesive-coated surface of the exfoliation sheet. Thus, a preferred kit 30 may include a small tube of lubricant 36. It may noted that comfortable exfoliation operations have been frequently carried out without the use of lubricant. For example, accidental removal of eyebrow hair is rare because these hairs grow out at an angle closely matching the preferred parting angle.

An exfoliation kit 30 of the invention may, in a preferred embodiment, comprise a plurality of adhesive-coated pre-cut exfoliation sheets 20 having backing sheets temporarily disposed thereon, a handle means 24 selected to have substantially the same length as an edge of ones of the sheets, a supply of lubricant or other masking material 36, a skin quantity comparison sheet 28 separate from or attached to ones of the sheets, and a suitable display package 38. The display package 38 may conveniently be a blister package comprising a cardboard back 40 and a transparent plastic blister overlay 42.

Although the present invention has been described with respect to several preferred embodiments, many modifications and alterations can be made without departing from the invention. Accordingly, it is intended that all such modifications and alterations be considered as within the spirit and scope of the invention as defined in the attached claims.

What is claimed is:

1. In a method for exfoliating a portion of epidermis from a selected portion of a user's body by adhering thereto a flexible exfoliant sheet having an adhesive on a surface thereof and by then removing the sheet from the selected portion of the body, an improvement comprising:
   a) selecting an exfoliant sheet having a size and shape adapted to fit the selected portion of the user's body;
   b) adhering, by means of the adhesive, a rigid handle to the sheet so that the handle extends along an edge of the sheet;
   c) adhering the sheet to the selected portion of the body; and
   d) grasping the handle and removing the sheet by pulling it along the selected portion of the body.

2. A method of exfoliating a portion of epidermis from a selected portion of a human body to remove a blemish therefrom, the method comprising the steps of:
   a) removing a backing sheet from one of a plurality of flexible exfoliation sheets to expose a respective adhesive-coated surface;
   b) applying the adhesive-coated surface of the flexible exfoliation sheet to the selected portion of the body;
   c) pulling the sheet along the selected portion of the body so as to remove the sheet therefrom;
   d) visually inspecting the selected portion of the body to determine if the blemish has been removed therefrom; and
   e) repeating steps a) through d), using a different one of the plurality of the exfoliation sheets on each repetition until observing, in one of the repeated steps d), that the blemish has been removed.

3. The method of claim 2 wherein step b) is carried out by a user who initially uses his or her fingers to press on that portion of the sheet adjacent an edge thereof and to thereafter rub his or her fingers away from the edge and over the sheet.

4. The method of claim 2 wherein, in step c), the edge of the sheet is held in contact with an adhesive-free surface of the exfoliation sheet while the sheet is being removed from the selected portion of the body.

5. The method of claim 2 further comprising a step, prior to applying the exfoliation sheet to the body, of attaching a handle to an edge of the sheet.

6. A method of exfoliating a portion of epidermis from a selected portion of a human body, the method comprising sequentially executed steps of:
   a) applying one of a plurality of flexible transparent exfoliation sheets, each of the sheets having a respective adhesive layer disposed on one of two surfaces thereof, to the selected portion of the body;
   b) holding a portion of the exfoliation sheet adjacent an edge thereof and pulling the sheet along the selected portion of the body so as to remove the sheet therefrom;
   c) visually inspecting the removed exfoliation sheet to determine an amount of exfoliated tissue adhering to the sheet;
   d) repeating steps a) through c), using a different one of the plurality of transparent exfoliation sheets for each repetition, until the amount of exfoliated tissue determined in one of the repeated steps c) is less than the amount of exfoliated tissue determined in the immediately previous repetition of step c).

7. The method of claim 6 wherein step a) is carried out by a user who initially uses his or her fingers to press on that portion of the sheet adjacent the edge and to then press on the rest of the sheet by moving his or her fingers away from the edge and over the sheet.

8. The method of claim 6 wherein, prior to step a), a handle is adhered to a portion of the one of the exfoliation sheets adjacent the edge thereof.

9. The method of claim 6 wherein, in step b), the edge of the sheet is held in contact with an adhesive-free surface of the exfoliation sheet while the sheet is being removed from the selected portion of the body.

10. The method of claim 6 wherein a single selected parting angle is used in each repetition of step b).

11. A kit for exfoliating a portion of epidermis from a selected portion of a human body, the kit comprising, in combination:

a plurality of flexible transparent sheets, each sheet having a surface coated with an adhesive, each sheet having at least one respective backing sheet adhered, by the adhesive, to the surface; and a handle adapted to be attached to an edge portion of one of the flexible sheets by means of the adhesive when one of the at least one respective backing sheets is removed therefrom.

12. The kit of claim 11 wherein the handle comprises a rod.

13. The kit of claim 11 further comprising a transparent comparison sheet having disposed thereon a plurality of visually distinct regions, each of the regions representative of a differing selected amount of exfoliated skin.

14. The kit of claim 11 wherein respective first and second backing sheets are adhered to the adhesive coated surface, the first respective backing sheet adhered to an edge portion of the respective flexible transparent sheet, the second respective backing sheet adhered to the remainder of the adhesive coated surface; and wherein the handle is adapted to be attached to the edge portion of the respective flexible transparent sheet when the respective first backing sheet is removed therefrom.

15. A method of exfoliating a portion of epidermis from a selected portion of a human body, the method comprising the sequential steps of:

a) applying one of a plurality of flexible transparent exfoliation sheets having an adhesive layer disposed on a surface thereof to the selected portion of the body;

b) holding a portion of the exfoliation sheet adjacent an edge thereof and pulling the sheet along the selected portion of the body so as to remove the sheet therefrom;

c) visually comparing the removed exfoliation sheet with a selected one of a plurality of visually distinct regions disposed on a transparent substrate, each of the regions respectively representative of a selected amount of exfoliated tissue; and d) repeating steps a) through c) until the comparison in step c) indicates that the appearance of the removed sheet matches that of the selected region.

16. The method of claim 15 wherein step a) is carried out by a user who initially uses his or her fingers to press on that portion of the sheet adjacent the edge and to then press on the rest of the sheet by moving his or her fingers away from the edge and over the sheet.

17. The method of claim 15 wherein a rigid handle is adhered to the portion of the exfoliation sheet adjacent the edge thereof prior to applying the one of the sheets to the body.

18. The method of claim 15 wherein, in step b), the edge of the sheet is held in contact with an adhesive-free surface of the exfoliation sheet while the sheet is being removed from the selected portion of the body.

19. The method of claim 15 wherein a single selected parting angle is used in each repetition of step b).

* * * * *